United States Patent
Arnold et al.

(10) Patent No.: US 10,072,290 B2
(45) Date of Patent: Sep. 11, 2018

(54) METHODS FOR AMPLIFYING FRAGMENTED TARGET NUCLEIC ACIDS UTILIZING AN ASSEMBLER SEQUENCE

(71) Applicants: Lyle J. Arnold, Poway, CA (US); Norman C. Nelson, San Diego, CA (US)

(72) Inventors: Lyle J. Arnold, Poway, CA (US); Norman C. Nelson, San Diego, CA (US)

(73) Assignee: AEGEA BIOTECHNOLOGIES, INC., Poway, CA (US)

( * ) Notice: Subject to any disclaimer, the term of this patent is extended or adjusted under 35 U.S.C. 154(b) by 251 days.

(21) Appl. No.: 14/773,366

(22) PCT Filed: Mar. 15, 2014

(86) PCT No.: PCT/US2014/029893
§ 371 (c)(1),
(2) Date: Sep. 7, 2015

(87) PCT Pub. No.: WO2014/145176
PCT Pub. Date: Sep. 18, 2014

(65) Prior Publication Data
US 2016/0068900 A1    Mar. 10, 2016

Related U.S. Application Data

(60) Provisional application No. 61/789,984, filed on Mar. 15, 2013.

(51) Int. Cl.
*C12Q 1/68* (2018.01)
*C12Q 1/6858* (2018.01)
*C12Q 1/6806* (2018.01)
*C12Q 1/6844* (2018.01)

(52) U.S. Cl.
CPC ......... *C12Q 1/6858* (2013.01); *C12Q 1/6806* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 2006/0194214 A1* | 8/2006 | Church | C12Q 1/6813 435/6.16 |
| 2008/0182296 A1* | 7/2008 | Chanda | C12N 15/1034 435/69.1 |
| 2012/0178129 A1* | 7/2012 | Li | C12N 15/1096 435/91.2 |

* cited by examiner

*Primary Examiner* — David C Thomas
(74) *Attorney, Agent, or Firm* — David B. Waller

(57) ABSTRACT

The present invention provides methods of amplifying a fragmented target nucleic acid containing short target nucleic acid fragments utilizing an assembler sequence to convert these short fragments into longer sequences enabling their identification and interrogation. This is particularly important when attempting to identify small genetic variations, such as SNVs, present in highly fragmented nucleic acid samples. Amplification is accomplished by hybridizing the short target nucleic acid sequences to the assembler sequence, where these short sequences serve as primers for extension. Since the fragmented target nucleic acids that contain SNVs are utilized as primers on the assembler sequence they are preserved during amplification and can be detected.

3 Claims, 2 Drawing Sheets

METHODS FOR AMPLIFYING FRAGMENTED TARGET NUCLEIC ACIDS UTILIZING AN ASSEMBLER SEQUENCE

CROSS-REFERENCE TO RELATED APPLICATIONS

This application is a non-provisional patent application of provisional patent application Ser. No. 61/798,984 filed Mar. 15, 2013 and claims the benefit of the filing date of PCT/US2014/029893 filed 15 Mar. 2014 under 35 U.S.C. § 371 from which the PCT application claims priority.

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION

(1) Field of the Invention

The present invention relates to methods of amplifying a fragmented target nucleic acid comprising short nucleic acid fragments. Specifically, methods that assemble and extend these short nucleic acids utilizing an assembler template to produce larger amplicons for further manipulation.

(2) Description of Related Art

There are many sample types where the target nucleic acids are heavily degraded making it difficult for standard molecular diagnostic assays to detect. More specifically, these target nucleic acids are shorter than the "foot-print" of the assays used to detect them. For example, to detect a target at very low copy number it is typical to amplify the target. Additionally, in many cases it is desired to detect the target with a very high degree of specificity. Frequently, this is at the resolution of a single nucleotide change. When amplification is employed, as with PCR reactions, there is a forward primer, a reverse primer, and a detection probe. Generally, these primers and the detection probe are at a minimum about 20 nucleotides in length. Assuming that there is no overlap of the primers and probes, this would require that the target be at least 60 nucleotides in length to accommodate binding of these three elements (i.e. the assay's footprint). Furthermore, the desired single nucleotide variation (SNV) to be detected may occur anywhere within the target nucleic acid sequence. For reliable detection, the single nucleic acid alteration should be positioned within the amplified target nucleic acid (i.e., within a region of the amplicon that is interior to the primer binding sites) to allow for the probe to hybridize selectively to this region. This effectively increases the potential footprint of the assay to a minimum of approximately 100 nucleotides in length for this type of detection.

In many cases, detecting a known or unknown SNV within the target sequence requires that the fragment for interrogation be as much as 160 nucleotides in length. This is due in large part to the arrangement of probes, primers, and blocking probes on the amplicons.

The challenge of this requirement is that many sample types contain fragments that are as short as 20-50 nucleotides in length, often due to partial degradation of the target DNA or RNA. This is typical of RNA sequences because they are more easily degraded. This is also common for particular types of samples, such as for urine and blood samples as well as for FFPE (formalin fixed paraffin embedded) and FNA (fine needle aspirate) samples where the associated nucleic acid becomes more degraded upon storage. In the case of urine, nucleic acids that have found their way into urine due to transrenal processing are by nature small in fragment size. Generally, nucleic acid fragments that pass through the kidney are about 20-50 nucleotides in length or even smaller.

Consequently, there is a need to expand the length of short target fragments to allow for more efficient and accurate detection. This requires that the expanded target short fragments possess the same sequence context as the sequence from which the short fragments were originally derived to enable proper interrogation. The present invention provides methods for fulfilling this need.

BRIEF SUMMARY OF THE INVENTION

The present invention provides methods for amplifying a fragmented target nucleic acid utilizing an assembly template that combines and extends short nucleic acid fragments of a target nucleic acid to produce larger amplicons for further manipulation.

One aspect of the present invention is a method for amplifying a fragmented target nucleic acid containing short target nucleic acid fragments that because of their length may be difficult to amplify using existing technologies. In one embodiment, the fragmented target nucleic acid is mixed with an assembler sequence that has a sequence substantially complementary, but differs in significant ways from the target nucleic acid. A collection of short target nucleic acid fragments are annealed to the assembler sequence and the short target nucleic acid fragments are extended by polymerase in the 3' direction to produce a collection of first duplex nucleic acids containing a collection of first nucleic acids and the assembler sequence.

The collection of first duplex nucleic acids is disassociated from the assembler sequence. The collection of first nucleic acids is annealed to a first primer having a sequence the same as a region of the assembler sequence that is to the 5' side (assembler sense) of the target region to be interrogated. In some cases, the primer site is located at the very 5'-terminus of the assembler sequence. The primer is extended in its 3' direction to produce a collection of second nucleic acids. The first and second nucleic acids are dissociated and again annealed to the assembler sequence as well as with each other and extended in their respective 3' directions by polymerase. This step is repeated, thereby extending and linearly amplifying the short fragmented target nucleic acids within the boundaries created by the first primer on the 5' side of the assembler sequence and the target nucleic acid fragment that is complementary to the 3' most region of the assembler sequence.

In a second aspect, once assembly has been achieved, the method further comprises detecting genetic variants specific to the target sequence, by using assay methods that are capable of detecting rare genetic events, in the presence of the assembler sequence.

In one embodiment the assembler sequence is a wild type assembler sequence.

In a second embodiment, the assembler sequence is genomic DNA or a portion thereof specific to the target of interest. In some embodiments, the genomic DNA or portions thereof are human genomic DNA. In other embodiments, the genomic DNA or portions thereof are associated with specific organisms such as viruses, bacteria, parasites, and fungi.

In a third embodiment, the assembler may be a segment of the target nucleic acid sequence and/or other arbitrary but known sequences.

In a fourth embodiment, the assembler sequence harbors genetic variations to both mutant as well as wild type sequences. In this application, once assembled, either mutant (genetic variant sequences) or wild type sequences can be determined, using downstream analysis methods, the presence of a wild-type sequence relative to the assembler sequence, or a genetic variation relative to the assembler sequence. Also, in parallel reactions wild type and genetic variant copy prevalence, and/or copy numbers can be determined.

In all cases, the assembler is designed to interrogate a region of a target nucleic acid by enlarging short nucleic acid fragments of the target nucleic acid through 3' extension.

In a sixth embodiment, the assembler sequence is double stranded.

In a seventh embodiment, the assembly takes place under PCR conditions using both forward and reverse primers.

In an eighth embodiment, multiple linear cycles of amplification are used to linearly assemble short nucleic acid fragments without the opportunity of the assembler to amplify under exponential amplification conditions that would occur in the presence of both forward and reverse primers.

In a ninth embodiment, assembly is performed at lower temperatures to aid the ability of short nucleic acid to hybridize to the assembler. Once assembly has occurred the amplification temperature may be raised and other reagents added to support exponential amplification.

In a tenth embodiment, two assembler reactions are conducted using a primer 3' of the region of interest for interrogation, and in a separate reaction, a primer 5' of the region of interest to be interrogated. Once assembly has occurred in the two separate reaction mixtures, they may be combined for exponential amplification reaction using both forward and reverse primers.

In an eleventh embodiment, when the fragmented nucleic acid is present in more elevated concentrations, the assembler reaction may be conducted co-incidentally with polymerase chain reactions (PCR).

In another embodiment, the assembler is in 10, 100, 1,000, 10,000, or 100,000-fold excess over the expected concentration of the nucleic acid fragments for assembly.

Other aspects of the invention are found throughout the specification.

DETAILED DESCRIPTION OF THE INVENTION

Figure 1:
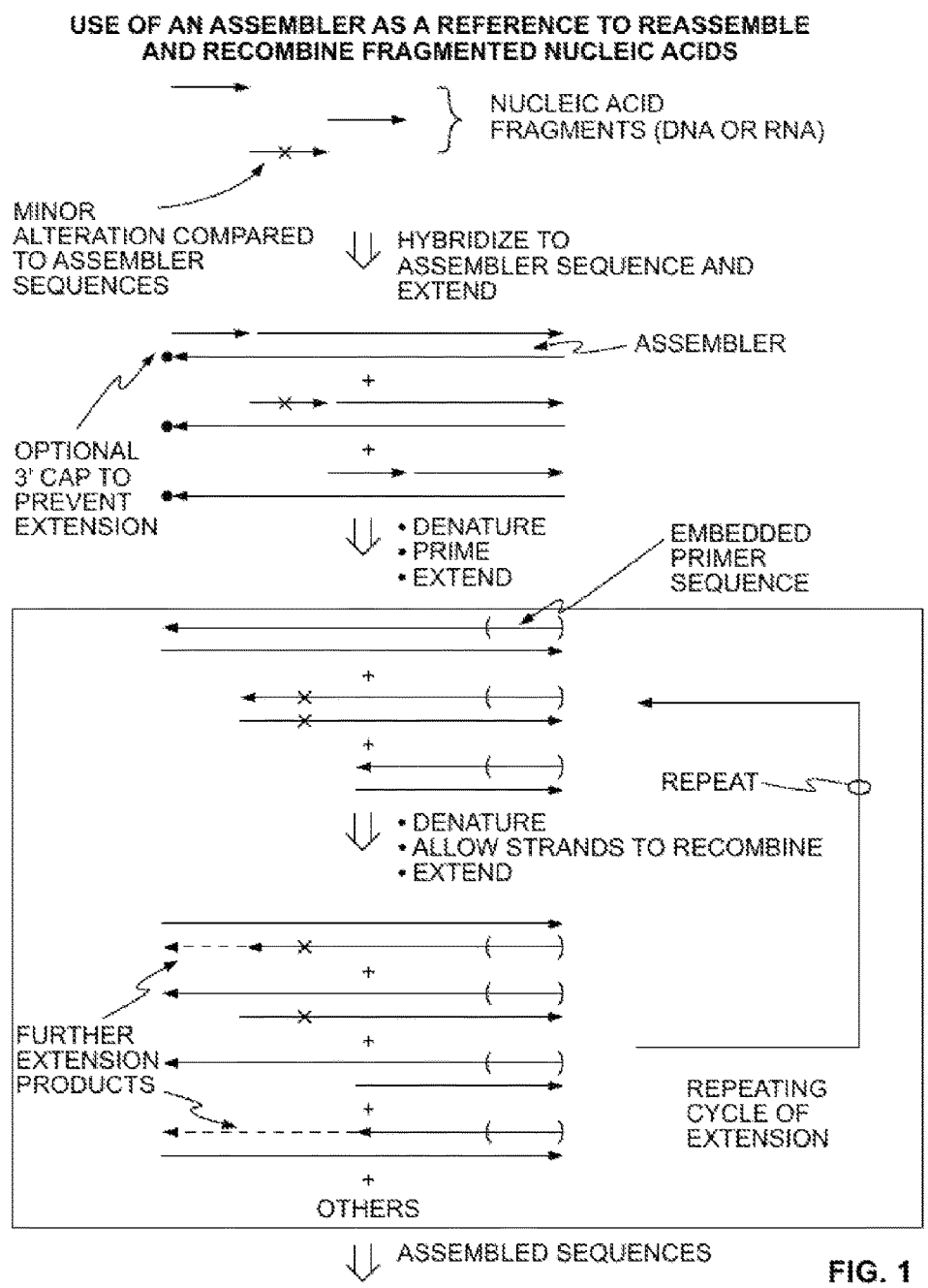
FIG. 1 is a schematic diagram of one aspect of the present invention.
Figure 1:
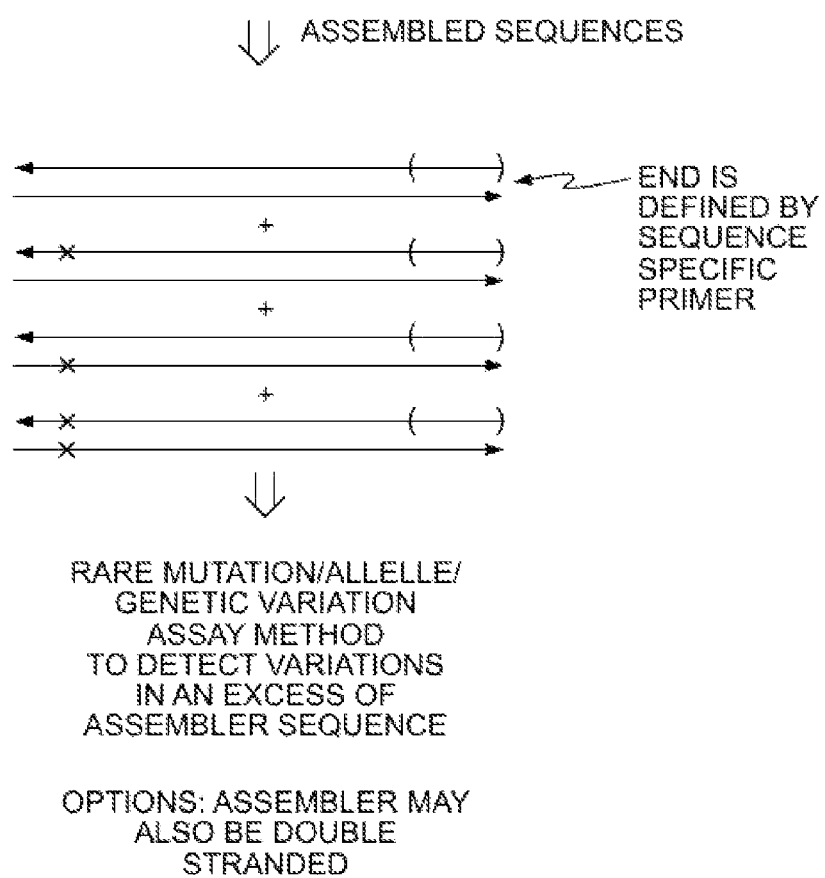

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "oligonucleotide" as used herein refers to a polymeric form of nucleotides, either ribonucleotides or deoxyribonucleotides, incorporating natural and non-natural nucleotides of a length ranging from at least 2, or generally about 5 to about 200, or more commonly to about 100. Thus, this term includes double- and single-stranded DNA and RNA. In addition, oligonucleotides may be nuclease resistant and include but are not limited to 2'-O-methyl ribonucleotides, phosphorothioate nucleotides, phosphorodithioate nucleotides, phosphoramidate nucleotides, and methylphosphonate nucleotides.

The term "target," "target sequence," or "target nucleic acid" as used herein refers to a nucleic acid that contains a polynucleotide sequence of interest, for which purification, isolation, capture, immobilization, amplification, identification, detection, quantitation, mass determination and/or sequencing, and the like is/are desired. The target sequence may be known or not known, in terms of its actual sequence and may be synthetic or obtained from a biological sample.

The term "primer" or "primer sequence" as used herein are nucleic acids comprising sequences selected to be substantially complementary to each specific sequence to be amplified. More specifically, primers are sufficiently complementary to hybridize to their respective targets. Therefore, the primer sequence need not reflect the exact sequence of the target. Non-complementary bases or longer sequences can be interspersed into the primer, provided that the primer sequence has sufficient complementarity with the sequence of the target nucleic acid to permit hybridization and extension.

In addition, primers may be nuclease resistant and include primers that have been modified to prevent degradation by exonucleases. In some embodiments, the primers have been modified to protect against 3' or 5' exonuclease activity. Such modifications can include but are not limited to 2'-O-methyl ribonucleotide modifications, phosphorothioate backbone modifications, phosphorodithioate backbone modifications, phosphoramidate backbone modifications, methylphosphonate backbone modifications, 3' terminal phosphate modifications and 3' alkyl substitutions. In some embodiments, the primer(s) and/or probe(s) employed in an amplification reaction are protected against 3' and/or 5' exonuclease activity by one or more modifications.

The skilled artisan is capable of designing and preparing primers that are appropriate for extension of a target sequence. The length of primers for use in the methods and compositions provided herein depends on several factors including the nucleotide sequence identity and the temperature at which these nucleic acids are hybridized or used during in vitro nucleic acid extension. The considerations necessary to determine a preferred length for the primer of a particular sequence identity are well known to the person of ordinary skill.

The term "blocker oligonucleotide" or "blocker" as used herein refers to a modified oligonucleotide or agent that binds to a nucleic acid or agent that binds to a modified nucleic acid that is capable of preventing or inhibiting replication and is incorporated into the primer(s) and/or probe(s) in an amplification reaction. Blocker oligonucleotides may include 2'fluoro (2'-deoxy-2'-fluoro-nucleosides) modifications, nuclease resistant nucleotides, or nucleotides with 3'-modifications all of which inhibit or prevent replication.

The term "sample" as used herein refers to essentially any sample containing the desired target nucleic acid(s), including but not limited to tissue or fluid isolated from a human being or an animal, including but not limited to, for example, blood, plasma, serum, spinal fluid, lymph fluid, tears or saliva, urine, semen, stool, sputum, vomit, stomach aspirates, bronchial aspirates, swabs (nasopharyngeal, rectal, ocular, urogenital, etc.), organs, muscle, bone marrow, FFPE tissue, skin, tumors and/or cells obtained from any part of the organism; plant material, cells, fluid, etc.; an individual bacterium, groups of bacteria and cultures thereof; food; cosmetics; drugs/pharmaceuticals; materials prepared via bioprocessing (finished product as well as intermediate materials); water; environmental samples, including but not limited to, for example, soil, water and air; semi-purified or purified nucleic acids from the sources listed above, for example; nucleic acids that are the result of a process, such as template formation for sequencing, including next generation sequencing, sample processing, nuclease digestion, restriction enzyme digestion, replication, and the like The term "amplifying" or "amplification" as used herein refers to the process of creating nucleic acid strands that are identical or complementary to a complete target nucleic acid sequence, or a portion thereof, or a universal sequence that serves as a surrogate for the target nucleic acid sequence.

The term "nucleic acid" or "nucleic acid sequence" as used herein refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof. In a nucleic acid, the backbone may be made up of a variety of linkages, including one or more of sugar-phosphodiester linkages, peptide-nucleic acid (PNA) linkages (PCT No. WO 95/32305), phosphorothioate linkages, methylphosphonate linkages, or combinations thereof. Sugar moieties in a nucleic acid may be ribose, deoxyribose, or similar compounds with substitutions, e.g., 2' methoxy and 2' halide (e.g., 2'-F) substitutions.

Nitrogenous bases may be conventional bases (A, G, C, T, U), non-natural nucleotides such as isocytosine and isoguanine, analogs thereof (e.g., inosine; The Biochemistry of the Nucleic Acids 5-36, Adams et al., ed., 11th ed., 1992), derivatives of purine or pyrimidine bases (e.g., $N^4$-methyl deoxyguanosine, deaza- or aza-purines, deaza- or aza-pyrimidines, pyrimidines or purines with altered or replacement substituent groups at any of a variety of chemical positions, e.g., 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, or pyrazolo-compounds, such as unsubstituted or 3-substituted pyrazolo[3,4-d]pyrimidine (e.g. U.S. Pat. Nos. 5,378,825, 6,949,367 and PCT No. WO 93/13121).

Nucleic acids may include "abasic" positions in which the backbone does not have a nitrogenous base at one or more locations (U.S. Pat. No. 5,585,481), e.g., one or more abasic positions may form a linker region that joins separate oligonucleotide sequences together. A nucleic acid may comprise only conventional sugars, bases, and linkages as found in conventional RNA and DNA, or may include conventional components and substitutions (e.g., conventional bases linked by a 2' methoxy backbone, or a polymer containing a mixture of conventional bases and one or more analogs). The term includes "locked nucleic acids" (LNA), which contain one or more LNA nucleotide monomers with a bicyclic furanose unit locked in a RNA mimicking sugar conformation, which enhances hybridization affinity for complementary sequences in ssRNA, ssDNA, or dsDNA (Vester et al., 2004, Biochemistry 43(42):13233-41).

The term "hybridization," "hybridize," "anneal" or "annealing" as used herein refers to the ability, under the appropriate conditions, for nucleic acids having substantial complementary sequences to bind to one another by Watson & Crick base pairing. Nucleic acid annealing or hybridization techniques are well known in the art. See, e.g., Sambrook, et al., Molecular Cloning: A Laboratory Manual, Second Edition, Cold Spring Harbor Press, Plainview, N.Y. (1989); Ausubel, F. M., et al., Current Protocols in Molecular Biology, John Wiley & Sons, Secaucus, N.J. (1994). The term "substantial complementary" as used herein refers both to complete complementarity of binding nucleic acids, in some cases referred to as an identical sequence, as well as complementarity sufficient to achieve the desired binding of nucleic acids. Correspondingly, the term "complementary hybrids" encompasses substantially complementary hybrids.

General methods for amplifying nucleic acid sequences have been well described and are well known in the art. Any such methods can be employed with the methods of the present invention. In some embodiments, the amplification uses digital PCR methods, such as those described, for example, in Vogelstein and Kinzler ("Digital PCR," *PNAS*, 96:9236-9241 (1999); incorporated by reference herein in its entirety). Such methods include diluting the sample containing the target region prior to amplification of the target region. Dilution can include dilution into conventional plates, multiwell plates, nanowells, as well as dilution onto micropads or as microdroplets. (See, e.g., Beer N R, et al., "On-chip, real time, single copy polymerase chain reaction in picoliter droplets," *Anal. Chem.* 79(22):8471-8475 (2007); Vogelstein and Kinzler, "Digital PCR," *PNAS*, 96:9236-9241 (1999); and Pohl and Shih, "Principle and applications of digital PCR," *Expert Review of Molecular Diagnostics*, 4(1):41-47 (2004); all of which are incorporated by reference herein in their entirety.) In some embodiments, the amplification is by digital PCR.

In some cases, the enzymes employed with the methods of the present invention for amplification of the target region include but are not limited to high-fidelity DNA polymerases, for example DNA polymerases that have 3'-5' exonuclease proof-reading capabilities. Examples of enzymes that can be used with the methods include but are not limited to AmpliTaq, Phusion HS II, Deep Vent, and Kapa HiFi DNA polymerase.

High-fidelity enzymes allow for high-fidelity (highly accurate) amplification of a target sequence. In some embodiments, the enzymes employed will include high-fidelity DNA polymerases, for example DNA polymerases that have 3'-5' exonuclease proofreading capabilities. Enzymes that can be used with the methods include but are not limited to AmpliTaq, Phusion HS II, Deep Vent, and Kapa HiFi DNA polymerase.

The amplification product can be detected/analyzed using a number of methods known to those skilled in the art including, but not limited to, fluorescence, electrochemical detection, gel analysis and sequencing. Furthermore, the product can be quantitated using a number of methods known to those skilled in the art such as real time amplification. Quantitation can be normalized by comparison to so-called "house-keeping genes" such as actin or GAPDH or to an internal control that can be added to the reaction in a known amount. Such methods are well known and have been described in Sambrook and Russell, *Molecular Cloning: A Laboratory Manual* (3rd Ed.) (2001).

Instrumentation for performing the methods described herein is readily available. Such instruments can include instruments for real-time and end-point PCR assays, emulsion PCR, solid-phase PCR, melting curve analyses, and sequencing analyses. Such instruments include Life Technologies 7500 Fast Dx real-time instrument (which is also capable of high-resolution melting curve analyses) and the 3500xl capillary gel instruments. Other instruments known in the art to be useful in the methods of the present invention are also contemplated for use by one of skill in the art in practicing the methods of the present invention.

The present invention provides methods for amplifying a fragmented target nucleic acid utilizing an assembler template that combines and extends short nucleic acid fragments of a target nucleic acid to produce larger amplicons for further manipulation and analysis. The target nucleic acid fragments may be DNA, RNA or a combination of the two.

In one aspect of the present invention, an assembly template or assembler sequence is utilized to convert short nucleic acid fragments into longer sequences to enable their identification and interrogation. This is particularly important when attempting to identify small genetic variations, such as SNVs, present in highly fragmented nucleic acid samples. This is accomplished by hybridizing the short target nucleic acid fragment sequences of interest with longer assembler sequences, where the short sequences serve as primers for extension. Since the fragmented target nucleic acids that contain SNVs are utilized as primers on the assembler sequence, the SNVs are preserved and can be detected.

For example, the method of the present invention provides for amplification of a fragmented target nucleic acid containing short nucleic acid fragments that, because of their length, may be difficult to amplify using existing technologies. The fragmented target nucleic acid is mixed with a single stranded assembler sequence that has a sequence substantially complementary to, but differs in significant ways from the target nucleic acid. A collection of short target nucleic acid fragments are annealed to the assembler sequence and the short target nucleic acid fragments are extended by polymerase in the 3' direction to produce a collection of first duplex nucleic acids containing a collection of first nucleic acids and the assembler sequence.

The collection of first duplex nucleic acids is disassociated from the assembler sequence. The collection of first nucleic acids is annealed to a first primer having a sequence the same as a region of the assembler sequence that is to the 5' side (assembler sense) of the target region to be interrogated. For example, if the region of interest is the EGFR gene associated with various mutations of medical significance, the first primer would be selected 5' (assembler sense) of the EGFR gene region to enable interrogation of these sequences that are in a 3' position (assembler sense) relative to the first primer. In some cases, the first primer site is located at the very 5'-terminus of the assembler sequence. The first and second nucleic acids are dissociated. The first and second nucleic acids then anneal to each other and they are extended from their 3'-termini with polymerase. Similarly, the first nucleic acids can also anneal to the assembler, in which case the first nucleic acids are extended from their 3'-temini with polymerase. Likewise, the first primer can also anneal to the first nucleic acids, in which case the first primer is extended from its 3'-temini with polymerase.

This step is repeated, thereby extending and linearly amplifying the short fragmented target nucleic acids within the boundaries created by the first primer on the 5' side of the assembler sequence and the target nucleic acid fragment that is complementary to the 3' most region of the assembler sequence. Several rounds of linear amplification (e.g. 10-15 rounds, or more) may be implemented as desired. Correspondingly, extended and re-extended sequences are able to recombine among themselves, as well as with the assembler sequence to extend their length and produce larger target nucleic acid sequences. If the primer is not located all the way at the 3' terminus of the assembler sequence, some extension products from the target nucleic acid fragments that will longer than boundaries described above.

The initial annealing step of the target nucleic acid fragments to the assembler sequence (or sequences if both strands are present) can be performed at lower temperature if desired to allow short target nucleic acid fragments to bind stably to the assembler. After the initial round or rounds of extension as described above, the temperature can be raised to complete the process as described above.

In another aspect of the present invention, a second primer is also provided that is the opposite sense of the first primer and is directed to the 3' side (assembler sense) of the target nucleic acid region to be interrogated. The second primer, however, can be no more 3' than the location of the 3' most fragment present in the mixture under analysis. The method proceeds as outlined above, but now the second primer will bind to second nucleic acids that are long enough to span the second primer binding site. Additionally, assembled fragments that become long enough to span both primer sites will be amplified exponentially.

In another aspect of this method, the assembler sequence is double stranded. In this case, the assembler is denatured and the target nucleic acid fragments are annealed to the complementary strand of the assembler (i.e., if the fragments are minus sense, they will anneal to the plus sense of the assembler, and vice-versa). The method will proceed as described above to produce first and second nucleic acids (if both senses of fragments are present, both senses of first nucleic acid will be produced; however, if the first primer is plus sense, only second nucleic acids of plus sense will be produced). At that point, the first and second nucleic acids are dissociated and annealed with each other (as the senses dictate), and/or the first nucleic acids are annealed to the plus strand of the assembler sequence, and/or the second nucleic acids are annealed to the minus strand of the assembler sequence, and/or the first primer will bind to the first nucleic acid (of the opposite sense) and the first and second nucleic acids and the first primer are extended in their respective 3' direction by polymerase. This step is repeated, thereby extending and linearly amplifying the short fragmented target nucleic acids.

In another aspect of this method, the assembler sequence is double stranded and a second primer is also utilized in the process. This second primer is analogous in design and use relative to the first primer, but designed relative to the other strand of the assembler sequence that is now present in the reaction mixture. The process proceeds as above except that in second nucleic acids of both senses will be produced and the both second nucleic acids will now bind to the opposite sense strand of the assembler and the second primer will now bind to the second nucleic of the appropriate sense. Repeating the steps of dissociation, annealing and extending will extend and linearly amplify the fragments. In addition, with both the first and second primers present, fragments that are assembled and become long enough to span both primer sites will amplify exponentially.

In another aspect of the method, both the plus and minus sense strands of the assembler are used, but the method of extending and linearly amplifying the target nucleic acid fragments is performed in two different tubes, one containing the plus sense assembler sequence and a plus sense first primer and one containing the minus sense assembler sequence and a minus sense second primer. After the reactions are completed, the contents of the tubes can be manipulated individually (e.g., amplified exponentially) or combined and manipulated together (e.g., amplified exponentially).

In another aspect of the method, one or more PCR reactions or one or more additional PCR reactions (if a first and second primer are already present) with primer pairs within the boundaries of the target nucleic acid to be interrogated can be conducted simultaneously with any of the assembler methods described above.

In the aspects above, the assembler strand or strands are present preferably at 10, 100, 1,000, 10,000, 100,000 or larger excess over the target nucleic acid fragments. In some cases the excess is less than 10-fold. In some cases, all or some of the fragments are present in excess over the assembler.

The assembler sequences are derived from the same genetic species as the fragmented target nucleic acids, and are highly related. For example, if the fragmented target nucleic acid being evaluated is human, within the region of interest the assembler sequence will contain very closely associated genomic target sequences. In some cases, the assembler is human genomic DNA or portions thereof. In other cases, the assembler sequence may be genomic DNA or portions thereof associated with specific organisms such as viruses, bacteria, parasites, and fungi. In some cases, the assembler is an arbitrary but known sequence.

The assembler sequence may be prepared from natural and synthetic sequences. Natural sequences include for example, genomic DNA, mRNA, plasmid DNA, and DNA or analogs thereof prepared using DNA synthesis. Synthetic sequences may be prepared DNA, RNA or analogs thereof, with the requirement that they serve as templates for DNA or RNA polymerase extension reactions. In one embodiment, human genomic DNA is used as the assembler sequence. In other embodiments, an equivalent human sequence is derived using DNA synthesis or cloning methodologies. Typically, the assembler sequence may contain slight genetic variations from both the wild type and mutant sequences, but retains sufficiently high sequence complementarity to hybridize with the fragmented target nucleic acids, so that specificity for the genetic sequence region from which the fragmented target nucleic acid is maintained.

In another embodiment the assembler sequence is a wild-type sequence that does not contain rare mutations such as SNVs. Utilizing a wild-type assembler sequence enables reliable detection of these mutations. In each case, the fragmented target nucleic acid sequence has adequate complementarity to allow hybridization to the assembler sequence with high specificity.

Once assembly has occurred according to the methods of the present invention, analysis of the now longer target nucleic acids can be performed using a variety of methods known in the art, both non-amplified and amplification-based, and including methods designed to detect rare genetic events and rare variants.

If the method used for subsequent analysis of the assembled target nucleic acids is amplification-based, such as PCR-based, for example, the amplification of the assembler sequence may be suppressed by a Selector assay described in U.S. Pat. App. No. WO/2012/151560. The Selector assay uses a blocker that suppresses wild-type sequences, while minimally effecting amplification of mutant sequences. The application of this assay allows rare mutations to be detected in "wild type" backgrounds where they may represent 0.1-0.01% percent or less the target species present. Thus using the Selector assay, mutant sites at a prevalence of 1:10,000 to 1 to 100,000 can be detected. The Selector assay may be utilized to suppress amplification of the assembler sequence whether it is a wild type sequence, or a variant of a wild-type sequence, as long as the assembler sequence is known or can be determined.

In some cases, the assembler sequence contains one or more SNVs compared with the target nucleic acid sequence. In another post assembly analysis method, a Selector like assay may be used to suppress amplification of the assembler sequence, while allowing amplification of SNVs associated of the short target sequence, and a separate assay may be used to detect the wild-type sequence, all while suppressing the assembler sequence. If one wants to know how much wild type is present as well as the amount of mutant, an assembler can be prepared that is a mismatch to both mutant and wild type. Possible mutant sequences can be assembled, as well as possible wild-type sequences. The assembler assembles both. A Selector assay (or equivalent) is constructed that suppresses the assembler, but doesn't suppress the mutant or the wild type. Allele specific Selector assays are then employed to determine the amount of mutant and the amount of wild type at individual SNV loci. Suppression is achieved utilizing a blocking oligomer specific for the region(s) of the assembler sequence that differs from the assembled sequences (e.g., regions where genetic variations of one or a few nucleotides are found.

Post assembly analysis methods may be performed in the presence of the assembler sequence or sequences, or the assembler sequence or sequences can be selectively removed from the mixture and analysis now performed in the absence of or in the presence of decreased levels of the assembler sequence or sequences. This yields further benefit to the analysis of the target nucleic acids by further increasing discrimination between the target nucleic acids and the assembler sequence or sequences. Methods to separate the assembler sequence(s) from the target nucleic acid sequences include but are not limited to, for example, size separation using methods known in the art (e.g. gel electrophoresis, spin columns, magnetic bead purification techniques, filtration and precipitation) when there is a distinguishable size differential between target nucleic acids and assembler sequence(s) or specific separation such as with biotin and streptavidin (for example, the assembler sequence(s) can be pre-labeled with biotin and, after assembly, removed from the mixture by specific capture with streptavidin-coated microspheres), digoxigenin and anti-digoxigenin antibody (for example, the assembler sequence(s) can be pre-labeled with digoxigenin and, after assembly, removed from the mixture by specific capture with anti-digoxigenin antibody-coated microspheres) or specific nucleic acid sequence capture (for example, a sequence(s) within the assembler sequence that is not related to the target nucleic acid sequences can bind to the complementary sequence(s) on microspheres and removed from the reaction mixture). Alternatively, the assembled target nucleic acid sequences can be labeled during the assembly process, such as, for example, via labeled nucleotide triphosphates or a labeled primer.

The information set forth above is provided to give those of ordinary skill in the art a complete disclosure and description of how to make and use the embodiments of the device and methods, and are not intended to limit the scope of what the inventor regards as his invention. Modifications of the above-described modes (for carrying out the invention that are obvious to persons of skill in the art) are intended to be within the scope of the following claims. All publications, patents, and patent applications cited in this specification are incorporated herein by reference. For example, many of the wash steps cited in the different methods are optional as are some of the steps that remove and/or separate two nucleic acid strands from one another. Not performing at least some of the wash and/or separation steps will afford a faster, simpler and more economical work flow, while still achieving the desired results. In another example, the stepwise addition/binding of certain oligonucleotides and/or target nucleic acids in the exemplified methods may be combined. Furthermore, a variety of polymerases, extension conditions and other amplification protocols known to those skilled in the art may be used in various steps or combination of steps in the methods described above. Other obvious modifications to the methods disclosed that would be obvious to those skilled in the art are also encompassed by this invention.

What is claimed is:

1. A method of amplifying a fragmented target nucleic acid containing target nucleic acid fragments, wherein said target nucleic acid has a region of interest for interrogation, said method comprising the steps of:
   (A) mixing said fragmented target nucleic acid with a longer and single assembler sequence, wherein said assembler sequence is substantially complementary to said fragmented target nucleic acid;
   (B) annealing said target nucleic acid fragments to said assembler sequence and extending said target nucleic acid fragments in the 3'-direction by polymerase to produce a collection of first duplex nucleic acids containing a collection of first nucleic acids and said assembler sequence;
   (C) disassociating said assembler sequence from said collection of first nucleic acids;
   (D) annealing a primer to said collection of first nucleic acids wherein said primer is substantially identical to a region of said assembler sequence and is located in a 3' orientation to the region of interest for interrogation, relative to the associated nucleic acid fragments, and extending said primer in the 3'-direction with polymerase to produce a collection of second duplex nucleic acids containing a collection of second nucleic acids and said collection of first nucleic acids;
   (E) dissociating said collections of said first and said second nucleic acids;
   (F) annealing said first and said second collection of nucleic acids with one another and said assembler sequence and extending said collection of said first and said second nucleic acids in the 3' direction; and
   (G) repeating steps E and F, thereby amplifying said fragmented target nucleic acid.

2. The method according to claim 1, wherein said assembler sequence is a wild type assembler sequence.

3. A method of amplifying and detecting a fragmented target nucleic acid containing target nucleic acid fragments, wherein said target nucleic acid has a region of interest for interrogation, said method comprising the steps of:
   (A) annealing said target nucleic acid fragments to a longer and single assembler sequence in a mixture comprising said target nucleic acid fragments and said assembler sequence wherein said assembler sequence is substantially complementary to said fragmented target nucleic acid and extending said target nucleic acid fragments in the 3'-direction by polymerase to produce a collection of first duplex nucleic acids containing a collection of first nucleic acids and said assembler sequence and optionally dissociating the said collection of first nucleic acids from said assembler sequence;
   (B) annealing a primer to said collection of first nucleic acids wherein said primer is substantially identical to a region of said assembler sequence and is located in a 3' orientation to the region of interest for interrogation, relative to the associated nucleic acid fragments, and extending said primer in the 3'-direction with polymerase to produce a collection of second duplex nucleic acids containing a collection of second nucleic acids and said collection of first nucleic acids and optionally dissociating said collection of second duplex nucleic acids;
   (C) annealing said first and said second collection of nucleic acids with one another and said assembler sequence and extending said collection of said first and said second nucleic acids in the 3' direction; and
   (D) repeating steps B and C, thereby amplifying said fragmented target nucleic acid; and
   (E) detecting the amplified target nucleic acid using an assay that is capable of detecting genetic variations down to the single nucleotide level.

* * * * *